United States Patent
Clifford, Jr. et al.

[11] Patent Number: 6,090,094
[45] Date of Patent: Jul. 18, 2000

[54] BALL VALVES AND USES THEREOF INCLUDING ENDOSCOPIC SURGICAL INSTRUMENTS

[75] Inventors: Richard A. Clifford, Jr., Worcester; Anthony J. Scappaticci, Bolton, both of Mass.

[73] Assignee: MicroGroup, Inc., Medway, Mass.

[21] Appl. No.: 08/726,149

[22] Filed: Oct. 4, 1996

[51] Int. Cl.[7] .................................................. A61M 31/00
[52] U.S. Cl. ............................................. 604/500; 604/28
[58] Field of Search ........................ 604/30, 32, 49–500; 251/315.12

[56] References Cited

U.S. PATENT DOCUMENTS

| | | | |
|---|---|---|---|
| 2,117,456 | 5/1938 | Schellin . | |
| 3,100,501 | 8/1963 | Hansen et al. | 137/454.6 |
| 3,223,111 | 12/1965 | Anderson | 137/454.6 |
| 3,434,691 | 3/1969 | Hamilton | 604/248 |
| 3,648,723 | 3/1972 | Nelson et al. . | |
| 3,735,956 | 5/1973 | Matousek | 251/315.12 |
| 3,827,439 | 8/1974 | Schulte et al. | 128/350 V |
| 4,026,516 | 5/1977 | Matousek | 251/315.12 |
| 4,184,510 | 1/1980 | Murry et al. | 604/30 |
| 4,263,897 | 4/1981 | Terayama . | |
| 4,397,617 | 8/1983 | Sergio et al. | 417/475 |
| 4,441,524 | 4/1984 | Mese | 251/315.12 |
| 4,567,880 | 2/1986 | Goodman | 128/7 |
| 4,573,498 | 3/1986 | Ludwig | 251/315.12 |
| 4,604,090 | 8/1986 | Reinicke | 604/118 |
| 4,668,215 | 5/1987 | Allgood | 604/30 |
| 4,681,560 | 7/1987 | Schulte et al. | 604/9 |
| 4,703,775 | 11/1987 | Pastrone | 604/32 |
| 4,819,637 | 4/1989 | Dormandy, Jr. et al. | 137/846 |
| 5,247,960 | 9/1993 | Kornfeldt et al. . | |
| 5,286,258 | 2/1994 | Haber et al. | 604/90 |
| 5,290,308 | 3/1994 | Knight et al. . | |
| 5,292,305 | 3/1994 | Boudewijn et al. . | |
| 5,312,332 | 5/1994 | Bales et al. | 604/49 |
| 5,322,503 | 6/1994 | Desai . | |
| 5,347,992 | 9/1994 | Pearlman et al. . | |
| 5,356,394 | 10/1994 | Farley et al. | 604/246 |
| 5,380,320 | 1/1995 | Morris | 606/33 |
| 5,490,836 | 2/1996 | Desai | 604/21 |

OTHER PUBLICATIONS

Product Literature, E/M Corporation.

*Primary Examiner*—Wynn Wood Coggins
*Assistant Examiner*—Jennifer R. Sadula
*Attorney, Agent, or Firm*—Peter F. Corless; William J. Daley, Jr.; Dike, Bronstein, Roberts & Cushman, LLP

[57] ABSTRACT

An on-off valve for medical procedures and laboratory devices, that has particular use with endoscopic medical procedures. Also featured are endoscopic devices that comprise such valves. The valve preferably includes a valve body, a valve member, a flexible seal member, a compression mechanism and a rotating mechanism. The body includes a centrally disposed cavity and two through apertures communicating therewith. The flexible seal member includes an internal chamber and two through flow apertures. The internal chamber is configured to rotatably receive the portion of the valve member including the internal flow passage. The seal member is mounted on the valve member and the seal/valve member assemblage is disposed in the body cavity. The compression mechanism acts on a surface of the seal member after it is disposed in the seal cavity so the seal member sealingly engages opposing surfaces of the valve member and the body. The rotating mechanism is interconnected to the valve member so that forces applied to a portion of the rotating mechanism cause the valve member to be selectively rotated in either a clockwise or counterclockwise direction. The seal member preferably includes a material coating to reduce the coefficient of friction between the valve member and the seal member and which has a melting temperature well above the temperatures used for sterilizing equipment/devices used in medical procedures.

12 Claims, 4 Drawing Sheets

BALL VALVES AND USES THEREOF INCLUDING ENDOSCOPIC SURGICAL INSTRUMENTS

FIELD OF THE INVENTION

The present invention relates to novel valves especially suitable for medical and laboratory use and, more particularly, valves adapted for use with endoscopic and laparoscopic surgical instruments.

BACKGROUND

In the course of endoscopic and laparoscopic surgical procedures, it is common to irrigate or suction an area within a patient to remove blood, vapors, and the like that result from the procedure. To control the flow of fluid into and out of the body, endoscopic and laparoscopic equipment includes ports, lines and the like which are interconnected to external equipment by on-off valves. The surgeon selectively actuates these valves to irrigate or suction the patient.

FIG. 1 shows a spring clip stopcock valve 10 that is designed for use in certain special procedures in hospitals and laboratories. That illustrated valve is exemplary of the types of valves presently used in connection with endoscopic and laparoscopic procedures. As shown in FIG. 1, spring clip stopcock valve 10 includes body 12, plug valve member 14, handle 16 and spring clip 18. Spring clip 18 is arranged about body 12 so as to retain the plug valve member 14 in the body.

Plug valve member 14 is frusto-conical in design and extends through apertures in the top and bottom of the body 12. Leak-tightness is attempted by maintaining close tolerances between the valve member and the body cavity receiving the valve member and through use of lubricating material to occlude space between opposing surfaces of those components. These prior valves however often leaked during use, creating an unclean and unsanitary environment and, more seriously, posing grave health concerns such as the transmission of HIV, hepatitis and the like to medical personnel.

These prior valves are routinely cleaned and sterilized for each use. Consequently, they require regular lubrication, typically prior to each use, clearly an inconvenient procedure. Use of a lubricant also often will result in undesired transmission of the lubricant material to a patient.

Further, because of the close tolerances between parts, these prior valves will typically leak more if replacement components are used. Thus, if a component requires replacement, the entire whole valve assembly is often disposed of rather than attempting to replace the defective component.

Other valves used for endoscopic and laparoscopic procedures are described in U.S. Pat. Nos. 4,263,897; 4,567,880; 4,668,215; 5,290,308; 5,292,305; 5,322,503; 5,347,992 and U.S. Pat. No. 5,490,836. In general the valves used are similar to those described above or are complex valve assemblies (e.g., spring loaded valves) involving numerous components.

There is therefore a need for simple valve assembly that at least minimizes, if not eliminates, the risk of leakage while yielding a valve that provides for smooth and easy operation. Moreover, there is a need for a valve which can be easily and simply repaired, cleaned and sterilized by the user. Further, there is a need for a valve that at least minimizes, and preferably does not require, the use of lubricants.

SUMMARY OF THE INVENTION

The present invention provides an on-off valve that is particularly useful in medical procedures and in laboratory devices. The valve of the invention essentially or even completely eliminates leakage and can be easily repaired, maintained, cleaned and sterilized.

Valves of the invention are especially useful with medical instruments, particularly endoscopic and laparoscopic procedures. The invention also provides medical instruments, particularly endoscopic and laparoscopic devices that comprises the described valve. Although the on-off valve of the instant invention is especially useful in connection with medical procedures, medical instruments and laboratory devices, this is not a limitation as to the possible uses for such a valve(s). For example, such valves can be used with any device, instrument and/or system, including those that use Luer fittings or tubing/tubing connections.

Preferred valves of the invention include a valve body, a valve member, and a flexible seal member, where the body includes a centrally disposed cavity and two through apertures that communicate with the cavity. The flexible seal member includes an internal chamber and two through-flow apertures. The internal chamber is configured to rotatably receive a portion of the valve member, the portion including the internal passage. The seal member is mounted on the valve member and the assembly of the flexible seal member and the valve member is disposed within the body cavity.

In specific embodiments, the seal member is made from BUNA-N material.

Further, the seal member hardness preferably lies in the range of from about SHORE A 30 to about SHORE A 60, more preferably a hardness of from about SHORE A 45 to about SHORE A 55. A hardness of about SHORE A 50 is particularly preferred.

The valve also includes a compression mechanism that acts on a surface of the seal member after it is disposed in the seal cavity. That mechanism compresses the seal member so it sealingly engages opposing surfaces of the valve member and the body. The valve further includes a rotating mechanism that is interconnected to the valve member. Forces applied to a portion of the rotating mechanism cause the valve member to be selectively rotated in either a clockwise or counterclockwise direction. The rotation of the valve member selectively opens and closes the valve.

In preferred aspects, the seal member includes a coating material on at least the surface of the seal member internal chamber so as to reduce the coefficient of friction between the valve member and the seal member. Further, the coating material preferably has a melt temperature well above the temperatures used for sterilizing equipment used in medical procedures.

In particularly preferred aspects, the coating is a permanent coating that is deposited or applied to the seal member. A permanent coating reduces or can eliminate the need to re-apply a material after each use of the valve as currently done with lubricating-type valves discussed above. A permanent coating also avoids transmission of a lubricating material to a patient. Preferred permanent coatings are polymers such as a poly(vinylphenyl) or other poly (aromatic) material. Parylene (e.g., parlyene N) is particularly preferred. A vacuum deposition or sputtering process is a preferred method for application of a permanent coating onto a seal member. Also, in less preferred aspects of the invention, any of a number of acceptable lubricants can be used in place of or in addition to a permanent coating.

Once assembled, a valve according to the instant invention is capable of withstanding fluid pressures of up to about 110 psig or more, or even 150 psig or more whereas prior art valves used with endoscopic instruments typically are limited to pressures on the order of about 40 psig. The seal member coating reduces the frictional forces between the valve member and the seal member so the valve member rotates smoothly thereby minimizing discomfort and possible injury to the patient. A permanent material coating, such as parylene N is also advantageous in that it does not lose its low coefficient of friction characteristic when subjected to sterilization and cleaning conditions used for surgical instruments.

Valves of the invention also can be easily disassembled and reassembled by a user without requiring special equipment or requiring detailed and complicated procedures. Further, a worn seal member can be easily removed and replaced with a fresh seal member to maintain a leak-tight condition of the valve.

DETAILED DESCRIPTION OF THE INVENTION

Figure 1:
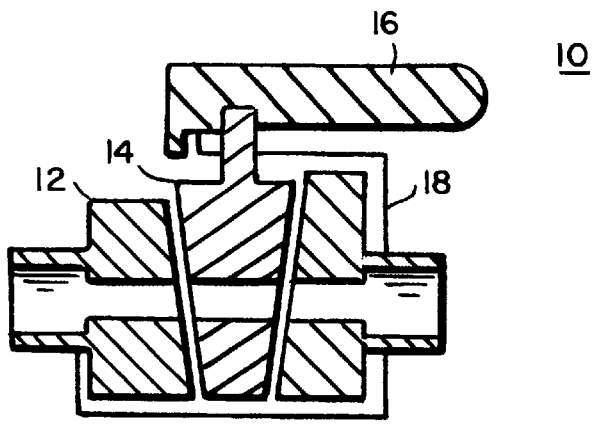
FIG. 1 is a cross sectional side view of a spring clip stopcock valve.
Figure 2A:
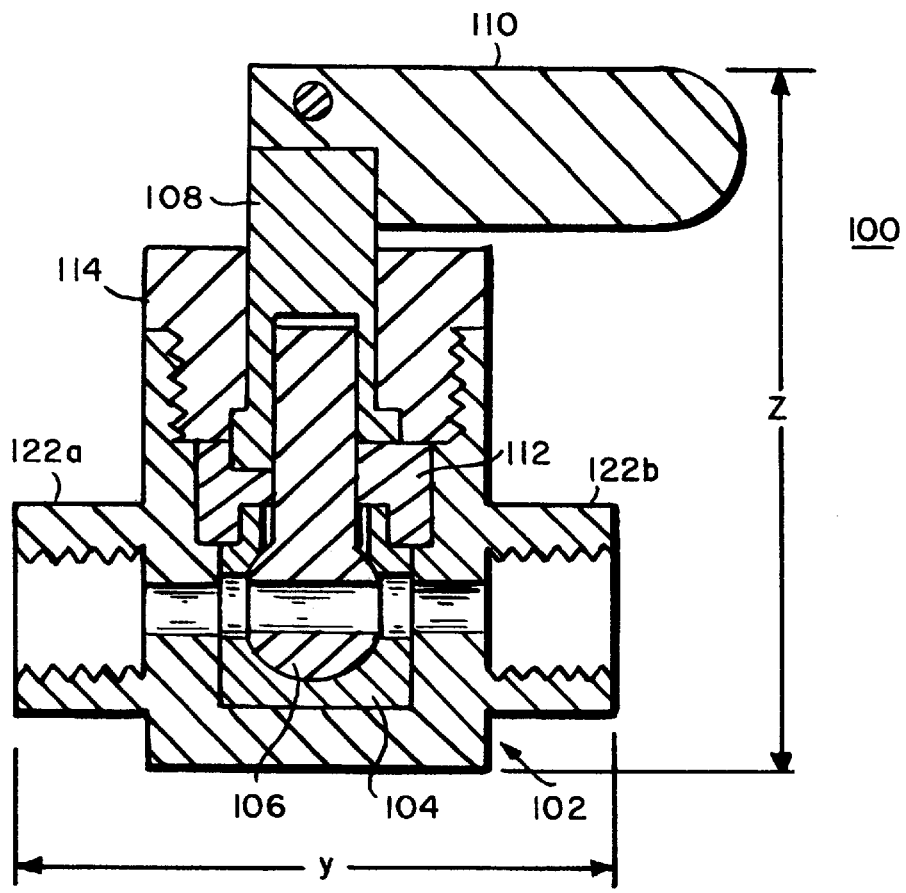
FIG. 2A is a cross sectional side view of a valve according to the instant invention.

Referring now to the various figures of the drawing wherein like reference characters refer to like parts, FIG. 2A shows a cross sectional side view of a preferred valve 100 according to the instant invention. Specific views for certain components of valve 100 also are shown in FIGS. 2B, 3A–B, 4A–C, 5A–C and FIGS. 6–7. As such, reference should be made to these figures in the following discussion. Also, references herein to an endoscopic instrument or procedure shall be understood to be generally inclusive of laparoscopic or other of the less invasive micro-surgery devices or procedures.

Figure 2B:
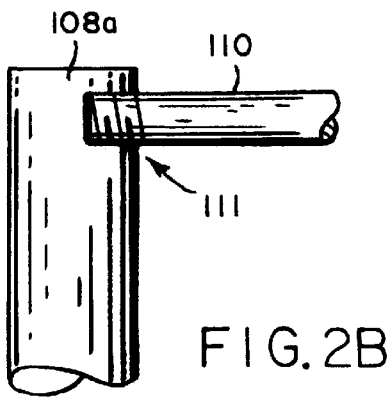
FIG. 2B is a cross sectional side view of an alternate handle/stem attachment for the valve of FIG. 2A.

Valve 100 preferably is a quarter-turn valve and includes body 102, seal member 104, valve member 106, valve stem 108 and handle 110. The valve stem and handle 110 are typically secured together by a pin passing through a hole 164 in the valve stem and a corresponding hole in the handle. However, the handle 110 can be secured to the stem 108 using any one of a number of available techniques. For example, as shown in FIG. 2B, a handle 110a can be secured to a stem 108a by means of a threaded connection 111.

In operation, handle 110 is rotated clockwise or counterclockwise (a quarter turn in the preferred quarter-turn embodiment) to selectively cause the valve member 106 to rotate in a similar fashion, thereby opening or closing the valve. The valve also preferably includes washer 112 and threaded cap 114 that cooperate, as discussed below, to compress the seal member 104 so it sealingly engages interior surfaces of the body 102 and exterior surfaces of valve member 106. In this way, a leak-tight condition is established.

In a preferred embodiment, body 102, valve member 106, valve stem 108, handle 110, washer 112 and cap 114 are stainless steel (e.g. 304 SS or 316 SS). Alternatively, any or all of these parts can be made from any of a number of biocompatible materials including plastics, that have the strength and chemical resistive properties for the intended use. For example, a rigid polypropylene could be employed. A rigid plastic may be preferred if the valve is intended for single use applications. Other metals also may be employed, but are generally less preferred than stainless steel.

Figure 3A:
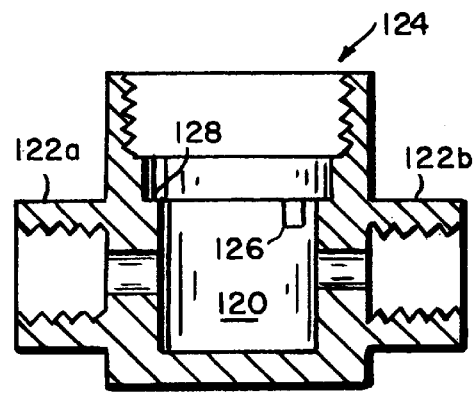
FIG. 3A is a cross sectional side view of the body for the valve of FIG. 2.
Figure 3B:
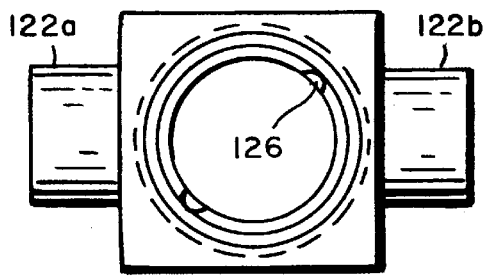
FIG. 3B is a top view of the body for the valve of FIG. 2.
Figure 4A:
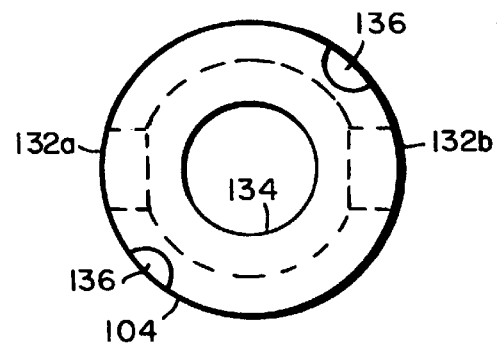
FIG. 4A is a top view of the seal member for the valve of FIG. 2.
Figure 4B:
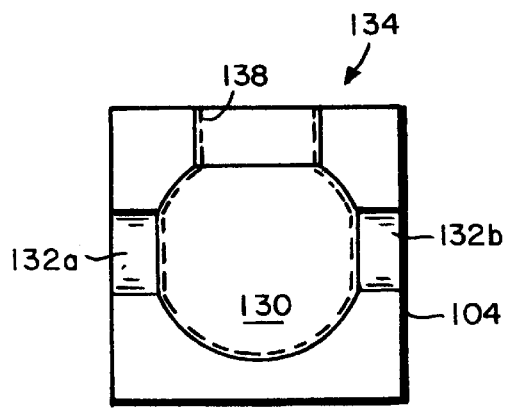
FIG. 4B is a cross sectional side view of the seal member of FIG. 4A.
Figure 4C:
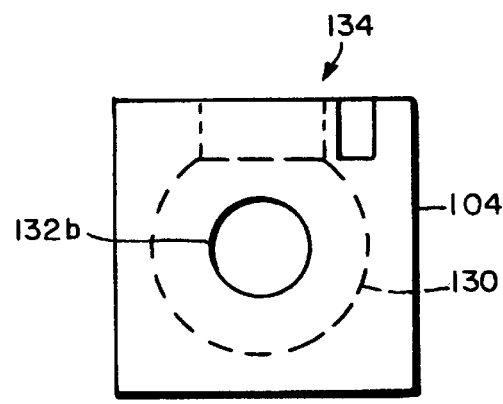
FIG. 4C is a side view of the seal member of FIG. 4A.

Body 102, as more clearly shown in FIGS. 3A,B, includes inlet and outlet connections 122a,b, which interconnect valve 100 to piping, tubing, endoscopic instrument or the like. Although these connections are illustrated as being threaded, each connection can be any of a number of connection types available and known to those skilled in the art. For example, the inlet and outlet connection 122a, can be configured with a male or female Luer connection detail. These connections 122a,b each include an internal flow passage that communicates with seal cavity 120 internal to valve body 102.

Valve body 102 also includes top opening 124 that communicates with seal cavity 120. The top opening is sized so an assembly comprising valve member 106 and seal member 104 can be introduced therethrough. The top opening includes a female thread connection to threadably engage the threads of cap 114. Alternatively, the top opening and cap can be configured so as to be secured to each other in any of a number of ways including a snap-lock type of connection. Preferably, the connection removably secures cap 114 to valve body 102 so the user can easily disassemble the valve 100 to replace any damaged or worn parts as well as to perform any desired maintenance activities. It is, however, within the scope of the instant invention for cap 114 to be secured in a permanent manner to the valve body 102.

Seal cavity 120 is configured to receive an assembly of the seal and valve members 104,106. Preferably, seal cavity 120 and seal member 104 are cylindrically shaped so an axial compression of the seal member causes a radial expansion of the seal member. Seal cavity 120 also is configured so its bottom and side surfaces sealingly engage the opposing surfaces of the seal member when the seal member is axially compressed therein. Thus, the configuration and cross-section of seal cavity 120 are established to make insertion of the valve/seal member assembly easy and simple yet assure that a leak tight connection can be made when the seal member is axially compressed. For example, in one embodiment, the difference between the inner diameter of the seal cavity and the outer diameter of the seal member is about 2 mils.

Seal member 104 preferably is a flexible, resilient, biocompatible material such as BUNA-N (Nitrile) having a hardness in the range of from about SHORE A 30 to about SHORE A 60 and more particularly a hardness of about SHORE A 50. Alternatively, seal member 104 can be any of a number of flexible materials such as a fluorocarbon such as VITON, neoprene(chloroprene) and the like that can be manufactured with the required shape and have the required material hardness or softness.

Seal member 104 includes an internal cavity 130 that is configured to generally conform to the spherical shape of the ball-end 150 of the valve member. The exposed surfaces of the seal member internal cavity 130 are coated with a material 138 to reduce frictional forces between valve member 106 and seal member 104 and thereby reduce the torque required to rotate the valve.

In a preferred embodiment, material 138 preferably is a bio-compatible material that is deposited or applied onto the seal member using any of a number of manufacturing techniques so as to essentially form a permanent coating. A vacuum deposition is particularly preferred. Material 138 preferably has a low coefficient of friction, as compared to that for the seal member material, and a melting temperature that is well above the temperatures typically used for sterilization (e.g., a melt temperature of at least about 20–30° C. greater than 135° C.). In a particular embodiment, the material coating 138 is a polymer such as a poly(vinylphenyl) or other poly(aromatic). More preferably, the polymer coating is parylene such as Parylene N.

A coating of Parylene N reduces the torque required to be developed for rotation by about 300–500% as compared to that required to rotate the valve member 106 in the "dry" or non-coated state. This makes the rotation of valve member 106 easy and smooth, thereby minimizing the potential discomfort or damage that could arise because of a sudden or erratic motion that might occur during the course of a surgical procedure.

The high melt temperature of parylene also allows valve 100 to be sterilized repeatedly without degrading the low frictional characteristic of the material. Thus, the valve with such a coating does not have to be disassembled and reassembled after sterilization or cleaning to establish the low friction condition. In contrast and as discussed above, prior valves typically require application of a lubricant after each cleaning procedure. Correspondingly, for non-medical applications the valve 100 can be operated at such temperatures without degrading the material's low frictional characteristic.

Although coating of seal member internal cavity 130 is illustrated, this is not a limitation. The amount of coverage of the coating is dependent upon a number of factors and considerations including simplification of the coating process, e.g., coating of all the exposed surfaces of seal member 104, and covering those surface(s) that would have a direct impact on minimizing the torque required to rotate the valve.

Alternatively, although less preferred, rather than use of such a permanent coating 138, a lubricant may be employed, for example vaseline, that is appropriate for the intended use and preferably having any required governmental approvals (e.g., FDA certification). Because of the simplified design for the valve 100 of the instant invention, the process of disassembling and re-assembling, including lubricating the valve, is simplified. Although generally unnecessary and less preferred, a lubricant also may be used in a valve that contains a permanent coating as discussed above.

As indicated above, seal member 104 is mounted on valve member 104 prior to insertion of the valve/seal member assembly into the body 102. This mounting is accomplished by passing valve member ball end 150 through the seal member top opening 134 so it passes into and remains disposed within seal member internal cavity 130. Seal member top opening 134 is sized so it is greater than or equal to the outer diameter of valve member stem portion 154 that extends therethrough. The resiliency of the material for seal member 104 allows seal member top opening 134 to deform so ball end 150 can pass therethrough and then return to the original configuration for seal member top opening 134.

Correspondingly, the resiliency of the material also allows seal member 104 to be easily dismounted from valve member 104. This makes the replacement of a worn seal member 104 by the user easy and simple. Also, because the seal member conforms to valve member ball end 150 following axial compression, a leak-tight condition is easily re-established by a replacement seal member 104. This is in contrast with known prior art valves that rely on tight tolerances and the presence of the lubricating medium to form a leak-tight condition. As discussed above, for such prior valves, replacement parts tend to make the valve prone to leakage more than that seen with originally manufactured valves.

To simplify the process of properly orientating seal member 104 and valve member 106 in valve body 102, valve body seal cavity 120 preferably includes at least one pair of diametrically opposed arcuate notches 126 and the seal member includes a pair of diametrically opposed arcuate notches 136. Arcuate notches 126 in the valve body seal cavity extend downward from internal lip 128 on which washer 112 rests when the valve is completely assembled. Seal member arcuate notches 136 extend downward from the top surface of seal member 104, the surface which comes into contact with a face 148 of washer disk 140.

Two diametrically opposed legs 146 also extend from this face 148 of washer disk 140. When the valve is completely assembled, as is illustrated in FIG. 2, these legs 146 engage the arcuate notches 126,136 in both valve body 102 and seal member 104. In this way, flow openings 132a,b in seal member 104 are aligned with the flow passages for the inlet and outlet connections 122a,b in the valve body 102. In addition to localizing and orientating seal member 104 within valve body 102, the engagement of legs 146 with arcuate notches 126,136 also assures that seal member 104 is restrained from movement while rotating valve member 106.

Figure 5A:
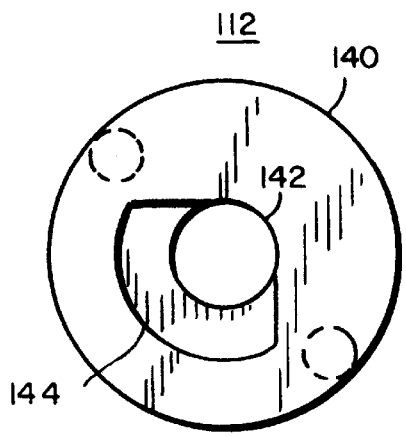
FIG. 5A is a top view of the washer for the valve of FIG. 2.
Figure 6:
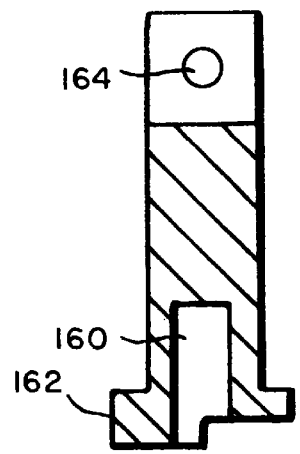
FIG. 6 is a cross sectional side view of the valve stem for the valve of FIG. 2.
Figure 5B:
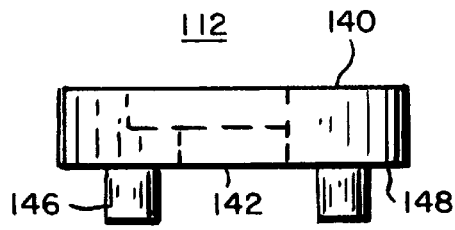
FIG. 5B is a side view of the washer of FIG. 5A.
Figure 5C:
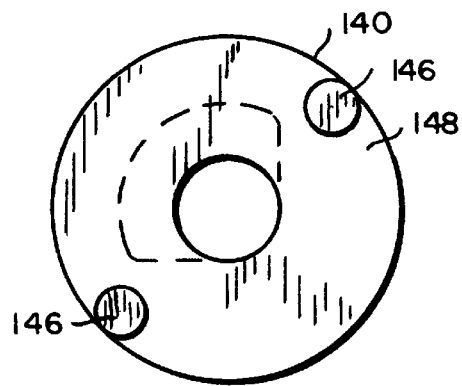
FIG. 5C is a bottom view of the washer of FIG. 5A.
Figure 7:
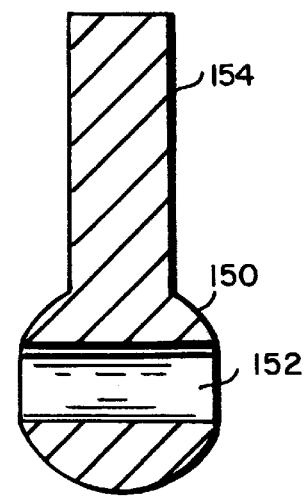
FIG. 7 is a cross sectional side view of the valve member for the valve of FIG. 2.

Legs 146 preferably are cylindrically shaped extensions from the surface 148 of the washer and each arcuate notch 136 in the seal member 104 preferably forms an essentially hollow cylinder with a corresponding notch 126 in the valve body seal cavity 120. Legs 146 can be arranged on surface 148 so they are stepped in from the outside diameter of disk 140 or lined up with the disk's outside diameter as illustrated in FIGS. 5A–C.

Washer 112 also preferably includes a depressed region 144 that generally corresponds to a 90° arc. The depressed region 144 cooperates with a finger portion 162 of stem 108 to control the rotation of the stem responsive to the rotary motion of handle 110. Simply, finger portion 162 engages the side walls of the depressed region 144 to limit rotational motion in either a clockwise or counterclockwise direction. Because valve member stem portion 154 is secured within the hollow portion 160 of stem 108, such as by an interference fit, valve member 106 also rotates responsively to the rotary motion of handle 110.

Depressed region 144 also is arranged on disk 140 with respect to the legs 146. Additionally, valve member 106 is secured to stem 108 so there is a set relationship between finger portion 162 and valve member internal passage 152. In this way, valve member internal passage 152 is localized and orientated with respect to the flow passages in the valve body inlet and outlet connections 122a,b when the legs 146 of washer 112 engage the valve body notches 126. This renders the user's re-assembly of the valve following maintenance activities simple and easy.

For purposes of maintenance activities, valve 100 of the instant invention can be broken down into two assemblies or groupings: valve body 102 and a valve/seal assembly that includes seal member 104, valve member 106, stem 108, handle 110, washer 112 and cap 114. To disassemble valve 100, a user unscrews cap 114 from valve body top opening 124 and removes the valve/seal assembly therefrom. The user then can perform whatever maintenance or repair activity is required, for example, the user replaces a worn seal member with a new one. As described above, a seal member is replaced by dis-mounting and mounting it on the valve member.

For reassembly, the user inserts the valve/seal assembly into the valve body top opening 124 and orientates the assembly so legs 146 are aligned with arcuate notches 126 in the valve body seal cavity 120. When the valve/seal assembly is properly orientated, the user screws cap 114 into top opening 124 until surface 148 of washer 112 contacts internal lip 128 of valve body 102.

As the user screws in cap 114, surface 148 of washer 112 also acts on the top surface of the seal member so as to axially compress the seal member 104 within the valve body seal cavity 120. The axial compression in turn causes seal member 104 to expand outwardly to sealingly engage the interior surfaces of seal cavity 120. Seal member 104 also expands inwardly towards valve member ball end 150 so as to sealingly engage the opposing surfaces of the ball end. That engagement establishes the leak-tight condition.

Re-assembly of valves of the invention is also convenient because parts may be readily interchanged after disassembly and cleaning without compromise of the sealing characteristics of the valve. In particular, the elasticity of seal facilitates interchange or replacement of ball and body components without reduction of sealing properties. In clear contrast, prior plug-type valves as discussed above require exact matching of components upon re-assembly to attempt to maintain desired sealing properties.

Figure 8:
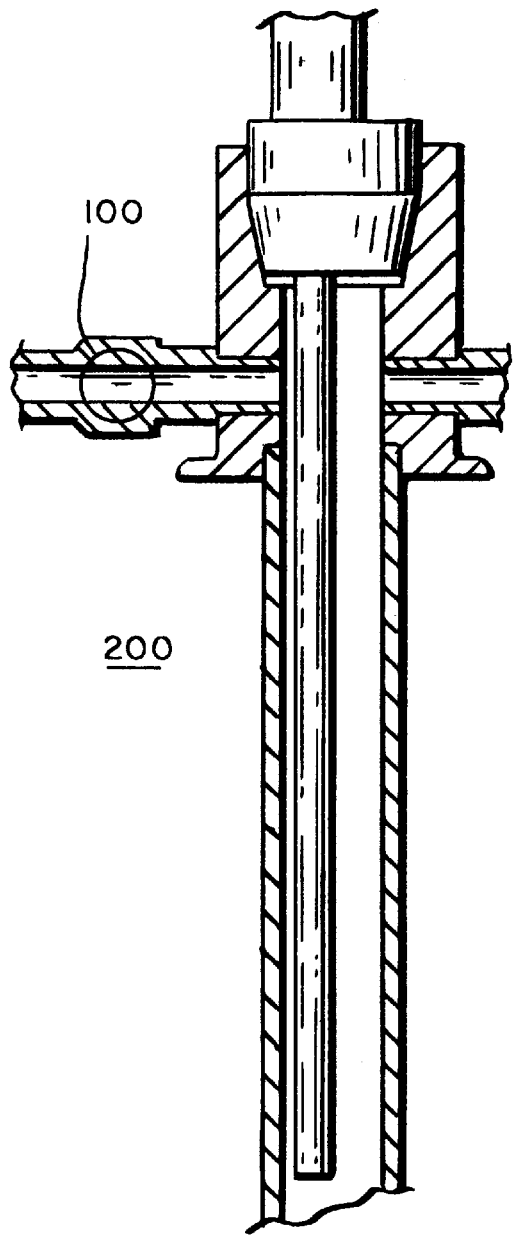
FIG. 8 is an exemplary endoscopic instrument with the valve of FIGS. 2A–2B.
Figure 9:
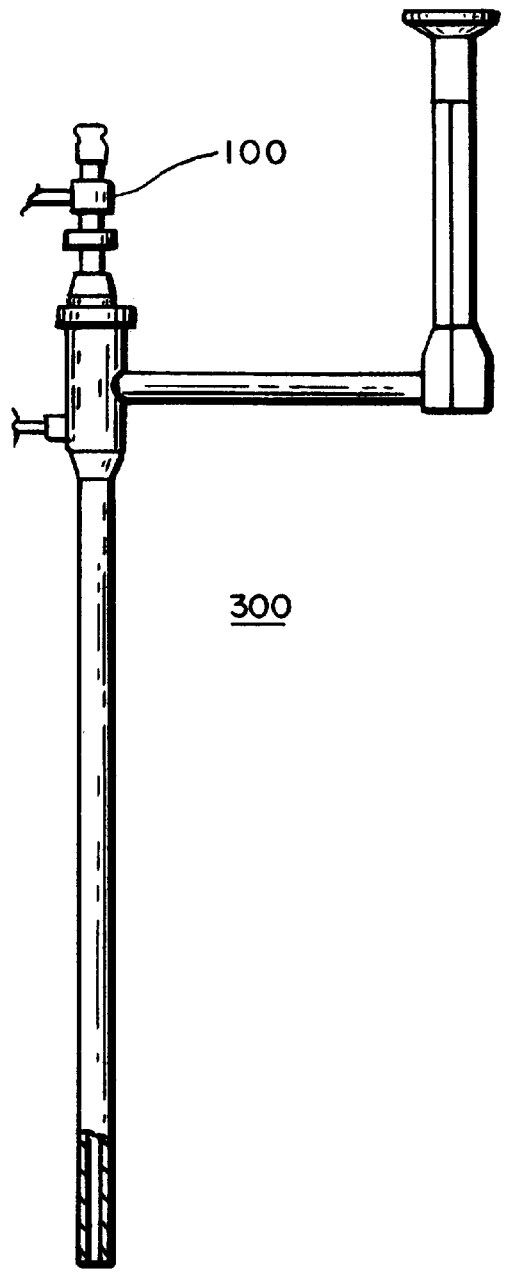
FIG. 9 is an exemplary laparoscopic instrument with the valve of FIGS. 2A–2B.

FIG. 8 shows an exemplary endoscopic instrument 200 of the invention, which comprises a valve 100 as described above. FIG. 9 shows an exemplary laparoscopic instrument 300, which also includes valve 100 of the invention. Flushing devices (irrigation and evacuation) are generally preferred endoscopic surgical instruments of the invention, wherein fluid flows through valve 100 both into and out of a patient. Also, separate valves of the invention can be used for irrigation and evacuation functions. Such devices are described in general in the above-mentioned U.S. patents, where the valve of the present invention may be substituted for a prior valve.

Although the valve 100 is illustrated as being used with specific instruments and correspondingly with specific procedures, the valve 100 can be used in any of a number of endoscopic procedures and with any of a number of instruments used in connection with these procedures.

In general, valves of the invention used for endoscopic procedures are small but can be easily operated by individuals. For these valves, the diameter of the spherical or ball end 150 of the valve member 106 suitably lies in the range of from about 80 to 170 mils, more preferably 90 to 160 mils. The diameter of the internal flow passage 152 therethrough lies in the range of from about 45 to 80 mils, more preferably 50 mils to about 80 mils.

For valves with other uses, such as in a laboratory, the diameter of the ball end and the internal flow passage suitably may be larger, for example a ball end 150 diameter of from 200 to 800 mils and a flow passage diameter of from about 100 to 250 mils. A 250 mil ball end diameter and a 130 mil diameter flow passage may be particularly suitable for laboratory applications, e.g. for transfer of solvents or other fluids. Larger valves also may be appropriate for laboratory use, e.g. an about 500 mils (i.e., ½ in.) ball end diameter with a correspondingly larger diameter flow passage.

A particularly preferred valve of the invention has a length (without adapter or connector fittings that may be employed as desired; length y in FIG. 2A) of ⅜ inches and width of ⅜ inches, a height (height z in FIG. 2B) of ⅞ inches, a ball end diameter of 156 mils and a 78 mil diameter flow passage.

Although the foregoing has described the valve of the instant invention in terms of its use as a valve for endoscopic instruments or procedures, this is not a limitation. It is within the scope of the instant invention for the above described valve to be used in connection with any medical procedure or device, for example, use with any irrigation device. Further, the valve of the instant invention can be used in laboratories for medical and non-medical tests or experiments. Moreover, the valve can be used with any device or in any system that uses Luer fittings/connections or tubing/tubing connections.

Valves of the invention can be manufactured by known procedures. For example, a stainless steel or other metal valve is suitable milled. A seven-axis CITIZEN machining center may be particularly suitable for milling production of a valve of the invention. A seal member may be suitably formed through a molding process. A plastic valve assembly may be suitably produced by an extrusion or an inset mold process, more typically a mold process. It also may be desirable to surface treat a valve, e.g. to subject a stainless steel or other metal valve to a passivation process such as a nitric acid treatment.

As should be clear from the above, valves of the invention preferably are non-integral with systems in which they are used, i.e. the entire valve assembly can be readily removed from a surgical or laboratory instrument or system such as by disconnecting tubing or a fitting.

While a preferred embodiment of the invention has been described using specific terms, such description is for illustrative purposes only, and it is to be understood that changes and variations may be made without departing from the spirit or scope of the following claims.

What is claimed is:

1. A method of irrigating or suctioning a patient in an endoscopic surgical procedure, comprising providing a rotating on-off ball-type valve in fluid connection with the patient, and manipulating the valve to selectively irrigate or suction the patient, wherein the valve comprises a body with a centrally disposed cavity a through aperture that communicates with the cavity; and a valve member having an internal passage, the valve member having a substantially ball-shaped end that fits within the body cavity, the body cavity conforming in shape to receive the valve member, and the valve member capable of rotating within the body cavity to selectively open or close the valve.

2. The method of claim 1 wherein the valve further comprises a seal member having an internal chamber, wherein the internal chamber is adapted to receive a portion of the valve member, and an assemblage of the seal member and the valve member is disposed within the body cavity.

3. The method of claim 2 wherein the valve further comprises a compression mechanism that acts on a surface of the seal member, where the compression mechanism compresses the seal member so it sealingly engages opposing surfaces of the valve member and the body.

4. The method of claim 2 wherein the seal member is at least partially coated with a material that reduces the coefficient of friction between the valve member and the seal member.

5. The method of claim 2 wherein the seal member has a hardness in the range of from about SHORE A 30 to about SHORE A 60.

6. The method of claim 2 wherein the valve contains a single seal member.

7. The method of claim 2 wherein the seal member is a unitary, integral member and is the sole seal component of the valve.

8. The method of claim 1 wherein the valve further comprises a rotating mechanism interconnected to the valve member, and the rotating mechanism is rotated to rotate the valve member to thereby selectively open or close the valve.

9. The method of claim 1 wherein the valve is a quarter-turn valve.

10. The method of claim 1 wherein the valve is connected to tubing.

11. The method of claim 1 wherein the ball-shaped end of the valve member has a diameter of from about 80 to 170 mils.

12. The method of claim 1 wherein the valve member is sealingly engaged within the valve body, and the valve member is rotated to selectively open or close the valve.

* * * * *